US010308584B2

(12) United States Patent
Dams et al.

(10) Patent No.: US 10,308,584 B2
(45) Date of Patent: Jun. 4, 2019

(54) METHODS OF MAKING (ALK)ACRYLIC ESTERS IN FLOW REACTORS

(71) Applicant: 3M INNOVATIVE PROPERTIES COMPANY, St. Paul, MN (US)

(72) Inventors: Rudolf J. Dams, Antwerp (BE); Rudy W. Van Campenhout, Hoboken (BE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 16/079,161

(22) PCT Filed: Feb. 21, 2017

(86) PCT No.: PCT/US2017/018633
§ 371 (c)(1),
(2) Date: Aug. 23, 2018

(87) PCT Pub. No.: WO2017/147040
PCT Pub. Date: Aug. 31, 2017

(65) Prior Publication Data
US 2019/0062257 A1      Feb. 28, 2019

Related U.S. Application Data

(60) Provisional application No. 62/299,575, filed on Feb. 25, 2016.

(51) Int. Cl.
*B01J 19/00* (2006.01)
*B01J 19/24* (2006.01)
*C07C 67/14* (2006.01)
*C07C 69/54* (2006.01)

(52) U.S. Cl.
CPC .......... *C07C 67/14* (2013.01); *B01J 19/0093* (2013.01); *B01J 19/248* (2013.01); *B01J 2219/0086* (2013.01); *B01J 2219/00889* (2013.01); *C07C 69/54* (2013.01)

(58) Field of Classification Search
CPC ...... C07C 67/14; C07C 69/54; B01J 19/0093; B01J 19/248; B01J 2219/0086; B01J 2219/00889
See application file for complete search history.

(56) References Cited

U.S. PATENT DOCUMENTS

| 1,951,782 | A | * | 3/1934 | Lauth | ................... | C08F 8/14 |
| | | | | | | 560/130 |
| 4,068,082 | A | | 1/1978 | Stoffey et al. | | |
| 4,258,204 | A | | 3/1981 | Banks et al. | | |
| 5,679,833 | A | | 10/1997 | Benn et al. | | |
| 5,808,148 | A | | 9/1998 | Gogate et al. | | |
| 6,192,596 | B1 | | 2/2001 | Bennett et al. | | |
| 6,228,434 | B1 | | 5/2001 | Affinito | | |
| 6,449,184 | B2 | | 9/2002 | Kato et al. | | |
| 7,351,339 | B2 | | 4/2008 | Maase et al. | | |
| 7,504,531 | B2 | | 3/2009 | Odell et al. | | |
| 8,148,567 | B2 | | 4/2012 | Ishiyama et al. | | |
| 2007/0255071 | A1 | | 11/2007 | Odell et al. | | |
| 2009/0023933 | A1 | | 1/2009 | Maase et al. | | |
| 2010/0185013 | A1 | | 7/2010 | Pinnow et al. | | |
| 2011/0071307 | A1 | | 3/2011 | Ishiyama et al. | | |
| 2011/0287991 | A1 | | 11/2011 | Dubois | | |

FOREIGN PATENT DOCUMENTS

JP         2003-137839         5/2003

OTHER PUBLICATIONS

Greene, T.W. et al.; "Greene's Protective Groups in Organic Synthesis"; Fourth Edition; A. John Wiley & Sons; 2007; 28 pages; including p. 222.
Hajipour, A.R. et al.; An Efficient and Simple Procedure for Preparation of Esters and Anhydrides From Acid Chlorides in the Presence of 1,4-Diazabicyclo[2.2.2]Octane (DABCO) Under Solvent-Free Conditions, Synthetic Communications, vol. 32; No. 1, 2002; pp. 23-30.
Ishihara, K. et al.; "An Extremely Simple, Convenient, and Selective Method for Acetylating Primary Alcohols in the Presence of Secondary Alcohols"; J. Org. Chem.; vol. 58; 1993; pp. 3791-3793.
Kikutani, Y. et al.; "Glass microchip with three-dimensional microchannel network for 2x2 parallel synthesis"; Lab on a Chip; vol. 2, 2002; pp. 188-192.
Naef, O. et al.; "Reaction Screening Using a Microreactor"; CHIMIA; vol. 64, No. 12; 2010; pp. 889-891.
Pipus, G. et al.; "Esterification of benzoic acid in microwave tubular flow reactor"; Chemical Engineering Journal; vol. 76; 2000; pp. 239-245.
Sano, T. et al.; "Remarkably Fast Acylation of Alcohols with Benzoyl Chloride Promoted by TMEDA"; Synthesis; No. 7; 1999; pp. 1141-1144.
Sinkovec, E. et al.; "Phase transfer catalyzed esterification: modeling and experimental studies in a microreactor under parallel flow conditions"; Microfluid Nanofluid; vol. 14; 2013; pp. 489-498.
Van Waes, F. et al. "Efficient and catalyst-free condensation of acid chlorides and alcohols using continuous flow"; Green Chem.; vol. 14; 2012; pp. 2776-2779.
Wiles, C. et al.; "Solution phase synthesis of esters within a micro reactor"; Tetrahedron; vol. 59; 2003; pp. 10173-10179.
Wiles, C. et al.; "Recent advances in micro reaction technology"; Chem. Commn.; vol. 47; 2011; pp. 6512-6535.
Yao, X. et al.; "Fast Esterification of Acetic Acid with Short Chain Alcohols in Microchannel Reactor"; Catal. Lett.; vol. 132; 2009; pp. 147-152.

\* cited by examiner

*Primary Examiner* — Pancham Bakshi
*Assistant Examiner* — Mark R Luderer
(74) *Attorney, Agent, or Firm* — Eric E. Silverman

(57) ABSTRACT

A method of making an (alk)acrylic ester in a microflow reactor.

15 Claims, No Drawings

METHODS OF MAKING (ALK)ACRYLIC ESTERS IN FLOW REACTORS

CROSS REFERENCE TO RELATED APPLICATIONS

This application is a national stage filing under 35 U.S.C. 371 of PCT/US2017/018633, filed Feb. 21, 2017, which claims the benefit of U.S. Provisional Patent Application No. 62/299,575, filed Feb. 25, 2016, the disclosure of which is incorporated by reference in its entirety herein.

BACKGROUND (Alk)acrylic esters have a variety of uses, such as monomers or co-monomers for making a variety of polymers. (Alk)acrylic ester can be produced industrially, such as by esterification of an alcohol with an (alk)acrylic acid under azeotropic conditions wherein water is removed from the reaction mixture during the reaction by distillation. This method is not useful for the manufacture of all (alk)acrylic esters, particularly those that are unstable at higher temperatures.

(Alk)acrylic esters can also be produced by addition of an alcohol to an (alk)acryloyl chloride. This reaction can be difficult to perform on an industrial scale because in order to proceed in good yield, it is necessary to rigorously exclude water from the reaction. Also, the reaction is highly exothermic, and therefore requires both very slow addition of the alcohol to the (alk)acryloyl chloride and effective cooling. Even with cooling, the reaction can pose a risk of fire or explosion when performed on an industrial scale

SUMMARY

A method of making an (alk)acrylic ester can include adding to a mixing chamber of a microflow reactor: (i) an alcohol; (ii) one or more bases that are sufficient to at least partially deprotonate the alcohol; (iii) a polar solvent; (iv) an (alk)acryloyl halide or a 3-haloalkylcarboxyl halide; and (v) an organic solvent that is immiscible with the polar solvent in sufficient quantity to dissolve the (alk)acryloyl halide or a 3-haloalkylcarboxyl halide. The molar flow ratio of the alcohol to the sum of all of the one or more bases is 1 to at least 1.1, such as 1 to at least 1.5. A product stream comprising one or more (alk)acrylic esters and one or more salts of the one or more bases is produced. The polar solvent that is added to the mixing chamber is sufficient to dissolve substantially all of the one or more salts. The product stream includes an organic portion and a polar portion, and the organic portion of the product stream comprises the (alk) acrylic ester in an amount of at least 80 wt % based on the total weight of the solutes in the organic portion of the product stream.

DETAILED DESCRIPTION

Throughout this disclosure, singular forms such as "a," "an," and "the" are often used for convenience; however, it should be understood that the singular forms are meant to include the plural unless the singular alone is explicitly specified or is clearly indicated by the context.

Some terms used in this application have special meanings, as defined herein. All other terms will be known to the skilled artisan, and are to be afforded the meaning that a person of skill in the art at the time of the invention would have given them.

Two or more liquids or solvents are "miscible" if they are soluble in each other in all proportions at room temperature and atmospheric pressure. Thus, two miscible liquids or solvents will form a solution when mixed in any ratio.

Two or more liquids or solvents are "immiscible" if they are not soluble in all proportions at room temperature and atmospheric pressure. Immiscible liquids or solvents may still have some solubility in one another. For example, diethyl ether can form a solution in water up to about 10% by weight, but is still immiscible in water since it does not form a solution in all proportions.

"Alkyl" refers to aliphatic hydrocarbon radical. Alkyl radicals can have any number of carbon atoms; the number of carbon atoms is often denoted in this disclosure by the notation "Cn" wherein "n" is an integer that corresponds to the number of carbon atoms. Thus, C1 means one carbon atom, C2 means two carbon atoms, C3 means 3 carbon atoms, etc. Typical alkyl groups are C30 or less, such as C26 or less, C24 or less, C22 or less, C20 or less, C18 or less, C16 or less, C12 or less C10 or less, C9 or less, C8 or less, C7 or less, C6 or less, C5 or less, C4 or less, C3 or less, or C2 or less. Many alkyl groups are C1 or greater, C2 or greater, C3 or greater C4 or greater, C5 or greater, C6 or greater, C7 or greater, C8 or greater, C9 or greater C10 or greater, C12 or greater, C14 or greater, C16 or greater, C18 or greater, C20 or greater, C22 or greater, C24 or greater, C26 or greater, or C28 or greater. Other alkyl radicals are also possible. Particular alkyl radicals are methyl. Other particular alkyl radicals are isooctyl. Other particular alkyl radicals are 2-octyldodecyl. Other particular alky radicals are 2-hexyl decyl.

"Alcohol" includes deprotonated alcohols as well as protonated alcohols.

"Halide," and other forms thereof, such as "halo," are used herein to refer to a chlorine, bromine, or iodine radical. Halides as used herein are most commonly chloride.

"(Alk)acrylic ester" or its plural refers to esters of acrylic acid or 2-alkylacrylic acid. Typically, an (alk)acrylic ester is an ester of acrylic acid or methacrylic acid.

"Hydroxy" refers to an OH radical.

"Carboxyl halide" refers to the carbon-centered radical O=C—X, wherein X is halide.

"Alkylcarboxyl halide" refers to a compound featuring a chemical bond between an alkyl radical of at least two carbon atoms and a carboxyl halide.

"3-Haloalkylcarboxyl halide" refers to an alkylcarboxyl halide bearing a halide radical that is covalently bonded to a carbon atom in the 3-position, i.e., the carbon atom in the beta position with respect to the carbonyl. The alkyl group is often a C2 alkyl group, and the 3-haloalkylcarboxyl halide is 3-halopropionyl halide, such as 3-chloropropionylhalide or 3-chloropropionyl chloride. The alkyl group in a 3-haloalkylcarboxyl halide can be substituted or unsubstituted; when substituted, however, there is at least one hydrogen atom bound to the carbon in the 2 position, i.e., the carbon atom in the alpha position with respect to the carbonyl. Typical substituents include alkyl, oxyalkyl, oxyalkyloxyalkyl, ether, aryl, heteroaryl, alkaryl, alkheteroaryl, oxyaryl, oxyheteroaryl, arylalkyl, heteroarylalkyl, oxyarylalkyl, oxyheteroarylalkyl, and the like. The alkyl group in 3-haloalkylcarboxyl halide can also be unsubstituted, which is more common.

"Acryloyl halide" means acryloyl chloride, acryloyl bromide, or acryloyl iodide.

"(Alk)acryloyl halide" means an acryloyl halide or an acryloyl halide bearing an alkyl radical covalently bonded to the carbon atom in the 3-position, i.e., the carbon atom in the beta position with respect to the carbonyl.

The "molar flow ratio" of two substances is the ratio of the flow rates of the two substances in mols of substance per unit time. A molar flow ratio can be calculated by one of skill in the art by dividing the concentration, in molarity, of each substance by its flow rate, then determining the ratio of the two resulting values. For example, if substance "X" is present in a liquid at a concentration of 2 mmol/mL and is flowing at a flow rate of 1 mL/min and substance "Y" is present in a liquid at a concentration of 4 mmol/mL and is flowing at a flow rate of 2 mL/min, then the molar flow ratio of X to Y is 1 to 1 (i.e. ((2 mmol/mL of X)/(1 mL of X/min)):((4 mmol/mL of Y)/(2 mL of Y/min)). When the molar flow ratio refers in part to an acid or a base, the moles of base are considered to be the moles of acidic or basic equivalents. Thus, if $Ca(OH)_2$ is present at in a liquid at a concentration of 2 mmol/mL and is flowing at a rate of 1 mL/min and an alcohol is present in a liquid at a concentration of 4 mmol/mL and is flowing at a rate of 2 mL/min, then the molar flow rate of the two is 2 to 1 (i.e. (2 mmol/mL of $Ca(OH)_2$×2 moles OH/mol $Ca(OH)_2$)/(1 mL $Ca(OH)_2$/min):((4 mmol/mL of Y)/(2 mL of Y/min)). Molar flow ratio is sometimes expressed as "N to at least M," wherein N and M are values. This notation means that the value M can be the stated value or greater. Thus, if the molar flow ratio of X to Y is "1 to at least 1," then the molar flow ratio can be 1 to any value that is 1 or greater, e.g. 1 to 1, 1 to 1.5, 1 to 2, 1 to 10, etc.

An (alk)acrylic ester can be made by a chemical reaction that takes place within a mixing chamber of a microflow reactor. An alcohol, one or more bases that are sufficient to at least partially deprotonate the alcohol, a polar solvent, an (alk)acryloyl halide or a 3-haloalkylcarboxyl halide, and an organic solvent that is immiscible with the polar solvent and present in sufficient quantity to dissolve the (alk)acryloyl halide or a 3-haloalkylcarboxyl halide can be added to the microreactor as the ingredients for this reaction.

Any microflow reactor can be used. Typically, the microflow reactor will have at least a first addition port and a second addition port for adding liquids to the mixing chamber of the microflow reactor. In many cases, further addition ports can be present. In many cases, only two, three, or four addition ports are used for adding material to the mixing chamber. When there are unused addition ports, the unused addition ports will typically be plugged so as to prevent the intake of any unwanted substances from outside the mixing chamber. One or more of the addition ports can have a check valve to prevent backflow, but this is not needed in most cases because the pressure of the reactant stream through the addition port is usually sufficient to prevent backflow. The mixing chamber of the microflow reactor will also typically have at least one exit port for a product stream to exit.

Some microflow reactors will have a mixing chamber with an internal volume of no more than 10 ml, such as no more than 5 mL, no more than 1 mL, no more than 900 μL, no more than 800 μL, no more than 750 μL, no more than 600 μL, no more than 500 μL, no more than 400 μL, no more than 250 μL, no more than 100 μL, or no more than 50 μL. The microflow reactor typically has a mixing chamber that has a geometry for promoting mixing of the ingredients added to the reactor chamber. In many cases, the mixing chamber can be designed to create a flowing plug of ingredients such that back-mixing of materials in the microflow reactor with materials later added to the microflow reactor is mitigated. The mixing chamber can have any suitable geometry, such as a T-shape, star-shape, circuitous tube shape, and the like. Suitable microflow reactors are commercially available, for example, under the trade designation IDEX 91 (ACHROM, Belgium) and LABTRIX START 1805-L-2 (Chemtrix BV, UK), the latter of which can be fitted with a glass microchip, such as those available under the trade designation TYPE 3223 (Chemtrix BV), which can function as the mixing chamber. Other microflow reactors have been described in U.S. Pat. Nos. 6,449,184, 6,228,434, and 6,192,596.

Impinging flow microreactors can be used. Such reactors are designed with addition ports that direct reactant streams to meet in a volume of the impinging flow reactor where they form a product stream. In such a case, the volume of the impinging flow reactor where the reactant streams meet is the mixing chamber. The pressure of the reactant streams through the inlet ports pushes the product stream through the mixing chamber and out of the exit port.

Any suitable alcohol can be used, so long as it contains at least one hydroxy radical that is capable of reacting with an (alk)acryloyl chloride, such as acryloyl chloride or methacryloyl chloride, under the reaction conditions in the microflow reactor. Typically, a monoalcohol having only one hydroxy radical is used. When a monoalcohol, with one hydroxy radical, is used, then the major reaction product can be a mono (alk)acrylic ester. Mono (alk)acrylic esters, which have only one ethylenically unsaturated group, are useful, for example, as monomers for making polymers. A poly alcohol, having two or more hydroxy radicals, can also be used. When a poly alcohol is used, then the major reaction product can be a poly (alk)acrylic ester. Such poly (alk) acrylic esters, with multiple ethylenically unsaturated groups, can be used, for example, as cross-linkers or curing agents.

In most cases, only a single alcohol is used. This is most common because, typically, the desired product is a single (alk)acrylic ester. However, it is also possible to use more than one alcohol. In such cases, the products will be a mixture of (alk)acrylic esters having different ester portions. The molar ratio of the different products will be similar to the molar ratio of the alcohols that are added to the mixing chamber of the microflow reactor. Making more than one (alk)acrylic ester at the same time in the same microflow reactor can be useful, for example, when the resulting mixture of (alk)acrylic esters is to be polymerized together into a single copolymer. In such a case, a product stream having a mixture of (alk)acrylic ester products can exit the microflow reactor, typically through the exit port, to form a product stream that can be fed directly into another reactor, for example, a reactor for polymerizing the mixture of (alk)acrylic ester products.

Many alcohols for use in the method will have a molecular weight of no more than 1 kilodalton, such as no more than 950 Daltons, not more than 900 Daltons, no more than 800 Daltons, no more than 750 Daltons, no more than 700 Daltons, no more than 650 Daltons, no more than 600 Daltons, no more than 550 Daltons, no more than 500 Daltons, no more than 450 Daltons, no more than 400 Daltons, no more than 350 Daltons, no more than 300 Daltons or no more than 250 Daltons. The alcohols used in this method can bear any functional group or substituent that does not interfere with the formation of the (alk)acrylic ester. Some common alcohols that can be used are 1-octanol, isooctyl alcohol, 2-ethyl hexyl alcohol, citronellol, 2-octyldodecanol, 4-hydroxybenzophenone, and 2-hexyldecanol.

The one or more bases can be any bases that are sufficient to at least partially deprotonate the alcohol. Typically, the one or more bases include an amine base. Common amine bases include trimethyl amine, dimethylethyl amine, triethyl amine, methyldiethyl amine, and the like. Triethyl amine is the most commonly used amine base. Alkali metal hydroxides, such as sodium hydroxide or potassium hydroxide, can also be used, either by themselves or in combination with an amine, such as triethyl amine. Alkali earth metal hydroxides, such as calcium hydroxide, can be also used although this is less common.

The polar solvent is commonly water, most often deionized water. Other solvents are occasionally used. When the solvent is not water, it is typically not an alcohol, or any other solvent that readily reacts with an (alk)acryloyl halide or a 3-haloalkylcarboxyl halide, since such solvents could take part in the reaction. An alcohol can be used as both the solvent and a reactant in some cases. Often the alcohol is mixed with water.

In most cases, the polar solvent will dissolve all or part of the one or more bases. Most commonly, the polar solvent will dissolve all of the one or more bases. This is particularly the case when the one or more bases are not liquids at the reaction temperature, typically room temperature. Thus, in most cases, the one or more bases will be added to the mixing chamber of the microflow reactor as a solution in the polar solvent, typically a solution in water. The most commonly used bases, alkali metal hydroxides and triethyl amine, are water soluble and therefore can be added to the mixing chamber of the microflow reactor in this manner. When a base is also soluble in the organic solvent, then it is possible to add that base as a solution in the organic solvent. When a base is a liquid at the reaction temperature, typically room temperature, then it is also possible to add that base neat, although this is not typical.

The alcohol reacts with at least one of (alk)acryloyl halide or 3-haloalkylcarboxyl halide inside the mixing chamber of the microflow reactor. In some cases, both an (alk)acryloyl halide and 3-haloalkylcarboxyl halide can be used, but this is not common. Most often, an (alk)acryloyl halide is used. Often, the (alk)acryloyl halide is an acryloyl halide. When an alkyl group is present, the alkyl group can be any alkyl group. Most commonly, the alkyl group is C10 or less, such as C9 or less, C8 or less, C7 or less, C6 or less, C5 or less, C4 or less, C3 or less, C2 or less, or C1. When the alkyl group is present, it is most often methyl. Thus, the most common (alk)acryloyl halides are acryloyl halide and methacryloyl halide. The halide is most commonly chloride, although bromide and iodide can be used. As such, acryloyl chloride and methacryloyl chloride are most common.

When a 3-haloalkylcarboxyl halide is used, the alkyl group is at least C2. The haloalkyl group are chosen such that the halogen and a hydrogen atom bound to the 2-carbon can be eliminated, such as by a beta-elimination process, to form an ethylenically unsaturated double bond in the presence of the one or more bases. Thus, the haloalkyl group is selected from those groups having at least one hydrogen atom bound to the 2-carbon atom, i.e., the carbon in the alpha position with respect to the carbonyl. Most commonly, the haloalkyl does not have any branching or substitutions at the 2-position. Commonly, the haloalkyl group is C30 or less, such as C26 or less, C24 or less, C22 or less, C20 or less, C18 or less, C16 or less, C12 or less, C10 or less, C9 or less, C8 or less, C7 or less, C6 or less, C5 or less, C4 or less, or C3 or less. The haloalkyl group is usually unsubstituted, but it can also be substituted. When substituted, the haloalkyl will have no more than one substituent attached to the 2-carbon atom, i.e., the carbon atom in the alpha position with respect to the carbonyl. Other carbon atoms have no such restrictions. Typical substituents include alkyl, oxyalkyl, oxyalkyloxyalkyl, ether, aryl, heteroaryl, alkaryl, alkheteroaryl, oxyaryl, oxyheteroaryl, arylalkyl, heteroarylalkyl, oxyarylalkyl, oxyheteroarylalkyl, and the like. The halo portion of the haloalkyl is most commonly chloro, but can be bromo or iodo. Similarly, the halide is most commonly chloride, although bromide or iodide can also be used. A typical 3-haloalkylcarboxyl halide is 3-chloropropionyl chloride.

The organic solvent is typically suitable for dissolving most if not all of the (alk)acryloyl halide or 3-haloalkylcarboxyl halide as well as most if not all of the (alk)acrylic ester reaction product. In addition, the alcohol typically has some solubility in the organic solvent in order to facilitate reaction with the (alk)acryloyl halide or 3-haloalkylcarboxyl halide. The organic solvent can also be suitable for dissolving all or part of the at least one base, but this is not necessary.

The organic solvent is conveniently immiscible with the polar solvent. This immiscibility facilitates separation of the (alk)acryl ester product, which is typically present largely in the organic solvent, from salts and other polar solvent soluble byproducts. Because the polar solvent is typically water, the organic solvent is typically immiscible with water. Exemplary organic solvents include dichloromethane, ethyl acetate, butyl acetate, methyl ethyl ketone, methyl butyl ketone, and the like. Dichloromethane is most common.

In practice, ingredients described herein are added to the mixing chamber of a microflow reactor. The addition is typically through at least two of the addition ports. Thus, the alcohol is typically added through a first port and the (alk)acryloyl halide or 3-haloalkylcarboxyl halide is added through a second port. Adding the alcohol through a different port than the (alk)acryloyl halide or 3-haloalkylcarboxyl halide prevents those reactants from undergoing a chemical reaction outside of the mixing chamber.

Most commonly, two addition ports are used. In such cases, the polar solvent, such as water, one or more bases, such as triethyl amine, and alcohol are typically added together through the first port. The mixture is most commonly added in the form of a solution wherein the one or more bases and alcohol are dissolved in the polar solvent. The (alk)acryloyl halide or 3-haloalkylcarboxyl halide and the organic solvent are typically added through the second addition port. Typically, the (alk)acryloyl halide or 3-haloalkylcarboxyl halide is dissolved in the organic solvent.

Three or four addition ports can also be used. When three addition ports are used, the alcohol, one or more bases, and polar solvent can be added, typically as a solution, through the first addition port, the (alk)acryloyl halide or 3-haloalkylcarboxyl halide can be added through a second addition port, and the organic solvent can be added through a third addition port. Alternatively, the alcohol and one or more bases can be added through the first addition port, the polar solvent can be added through the second addition port, and the (alk)acryloyl halide or 3-haloalkylcarboxyl halide and organic solvent can be added, typically as a solution, through the third addition port. When four addition ports are used, the alcohol and one or more bases can be added through the first addition port, the (alk)acryloyl halide or 3-haloalkylcarboxyl halide can be added through the second addition port, the polar solvent can be added through the third addition port, and the organic solvent can be added through the fourth addition port.

Other variations are also possible when three or more addition ports are used. In one such variation, the alcohol can be added in the organic solvent rather than in the polar solvent. In one example of this variation, the alcohol can be added as a solution in a first organic solvent through a first addition port, the (alk)acryloyl halide or 3-haloalkylcarboxyl halide can be added as a solution in a second organic solvent through a second addition port, and the one or more bases can be added as a solution in polar solvent, typically water, through a third addition port. The first or second organic solvents can be the same or different, and can be selected from any of the organic solvents discussed herein.

The product stream that exits from an exit port of the microflow reactor will typically have a polar portion and an organic portion. Because the polar solvent and the organic solvent are immiscible, the organic portion and polar portion are often present as two phases. The (alk)acrylic ester, along with any organic byproducts and unreacted alcohol, is typically present in the organic phase. Salts and polar-solvent soluble byproducts are typically present in the polar solvent portion. When the polar solvent includes water or is water, the polar solvent portion or polar solvent phase are an aqueous portion or aqueous phase. The polar phase and organic phase can be separated by known methods of separating polar and organic phases.

More than one microflow reactor can be used in parallel. For example, when two microflow reactors each having two addition ports are used, then a first reactant stream, for example containing the polar solvent, one or more bases, and alcohol, is split in two, and the two first reactant streams are added, respectively, to the first inlet port of the first microflow reactor and the first inlet port of the second microflow reactor. Similarly, a second reactant stream, for example containing the (alk)acryloyl halide or 3-haloalkylcarboxyl halide and the organic solvent, is split in two, and the two second reactant streams are added, respectively, to the second addition port of the first microflow reactor and the second addition port of the second microflow reactor. The product streams that exit the first and second microflow reactors can be kept separate, or can be combined into a single product stream.

The ingredients can be added to the mixing chamber of the microflow reactor at any suitable flow rate. The flow rate will vary depending on the internal volume and geometry of the mixing chamber. Exemplary flow rates are between 0.1 µL/min and 10 µL/min, for example greater than 0.1 µL/min, greater than 0.2 µL/min, greater than 0.3 µL/min, greater than 0.4 µL/min, greater than 0.5 µL/min, greater than 0.6 µL/min, greater than 0.7 µL/min, greater than 0.8 µL/min, greater than 0.9 µL/min, greater than 1.0 µL/min, greater than 1.1 µL/min, greater than 1.2 µL/min, greater than 1.3 µL/min, greater than 1.4 µL/min, greater than 1.5 µL/min, greater than 1.6 µL/min, greater than 1.7 µL/min, greater than 1.8 µL/min, greater than 1.9 µL/min, greater than 2.0 µL/min, greater than 2.1 µL/min, greater than 2.2 µL/min, greater than 2.3 µL/min, greater than 2.4 µL/min, greater than 2.5 µL/min, greater than 2.6 µL/min, greater than 2.7 µL/min, greater than 2.8 µL/min, greater than 2.9 µL/min, greater than 3.0 µL/min, greater than 3.25 µL/min, greater than 3.5 µL/min, greater than 3.75 µL/min, greater than 4.0 µL/min, greater than 4.5 µL/min, greater than 5.0 µL/min, greater than 5.5 µL/min, greater than 6.0 µL/min, greater than 6.5 µL/min, greater than 7.0 µL/min, greater than 7.5 µL/min, greater than 8.0 µL/min, greater than 8.5 µL/min, greater than 9.0 µL/min, or greater than 9.5 µL/min. Suitable flow rates can also be up to 10 µL/min, up to 9.5 µL/min, up to 9.0 µL/min, up to 9.0 µL/min, up to 8.5 µL/min, up to 8.0 µL/min, up to 7.5 µL/min, up to 7.0 µL/min, up to 6.5 µL/min, up to 6.0 µL/min, up to 5.5 µL/min, up to 5.0 µL/min, up to 4.75 µL/min, up to 4.5 µL/min, up to 4.25 µL/min, up to 4.0 µL/min, up to 3.75 µL/min, up to 3.5 µL/min, up to 3.25 µL/min, up to 3.0 µL/min, up to 2.9 µL/min, up to 2.8 µL/min, up to 2.7 µL/min, up to 2.6 µL/min, up to 2.5 µL/min, up to 2.4 µL/min, up to 2.3 µL/min, up to 2.2 µL/min, up to 2.1 µL/min, up to 2.0 µL/min, up to 1.9 µL/min, up to 1.8 µL/min, up to 1.7 µL/min, up to 1.6 µL/min, up to 1.5 µL/min, up to 1.4 µL/min, up to 1.3 µL/min, up to 1.2 µL/min, up to 1.1 µL/min, up to 1.0 µL/min, up to 0.9 µL/min, up to 0.8 µL/min, up to 0.7 µL/min, up to 0.6 µL/min, or up to 0.5 µL/min. Other flow rates may also be suitable, depending on the geometry and internal volume of the microflow reactor that is used. A person of skill in the art will be able to determine appropriate flow rates from the guidance provided herein, in combination with their knowledge of the art.

Selecting appropriate molar flow ratios of some of the components can be important in achieving optimal results. The term molar flow ratio is defined herein. The inventors have found that using the correct molar flow ratios can be critical for achieving the desired products in high yield. Thus, the molar flow ratio of the alcohol to the sum of all of the one or more bases is typically 1 to at least 1, at least 1.5, or 1 to at least 1.7, particularly when (alk)acryloyl halide, such as (alk)acryloyl chloride or (meth)acryloyl chloride, is used. In some cases, the molar flow ratio of the alcohol to the sum of all of the one or more bases can be even higher, such as 1 to at least 2, 1 to at least 2.5, or even 1 to at least 2.7. Such higher molar flow ratios are not required unless otherwise specified, but they are often beneficial when 3-haloalkylcarboxyl halide is used as a reactant.

The molar flow ratio of the alcohol to the (alk)acryloyl halide or 3-haloalkylcarboxyl halide is typically 1 to at least 1.1. When the molar flow ratio is lower, the amount of (alk)acrylic ester in the product stream is often unacceptably low. An even higher molar flow ratio can also be used in some cases. Thus, the molar flow ratio of alcohol to (alk)acryloyl halide or 3-haloalkylcarboxyl halide can be 1 to at least 1.2, 1 to at least 1.3, 1 to at least 1.4, 1 to at least 1.5, 1 to at least 1.6, 1 to at least 1.7, 1 to at least 1.8, 1 to at least 1.9, 1 to at least 2, 1 to at least 2.1, 1 to at least 2.2, 1 to at least 2.3, 1 to at least 2.4, or 1 to at least 2.5. Such higher molar flow ratios are not required unless otherwise specified.

When a poly alcohol having more than one hydroxy radical per molecule is used, in order to react each hydroxy radical with a molecule of the (alk)acryloyl halide or 3-haloalkylcarboxyl halide, the molar flow ratio discussed above can be used, except that the molar flow ratios would be based on mol equivalents of hydroxy radical rather than mols of poly alcohol.

In the microflow reactor, the reaction of the alcohol and (alk)acryloyl halide or 3-haloalkylcarboxyl halide typically produces one or more salts of the one or more bases.

If these salts precipitate, they can clog the microflow reactor causing a process failure. Thus, the polar solvent, which is typically water, must be present in sufficient quantity to dissolve substantially all of the salts. In this context, "substantially all" means that enough salt is dissolved such that any undissolved salt does not clog the microflow reactor during the process. The flow rate necessary to achieve this result can vary greatly and depends on the volume and geometry of the particular microflow reactor that is used. Following the guidelines herein in combination with their knowledge of the art, a person of ordinary skill in the art will be able to determine a proper flow rate of polar solvent, such as water, in order to assure that all of the salts are dissolved. Thus, if salts clog the microflow reactor at a particular flow rate, the problem can be ameliorated in several ways. If the polar solvent is being added as the solvent of a solution, for example, having alcohol, one or more bases, or both as solute, then the flow rate of this solution can be increased or the concentration of the solute or solutes decreased. If neither of these is feasible, for example, because of the requirement to maintain an appropriate molar flow ratio or for other reasons, then the clogging problem can be ameliorated by using more than two addition ports and adding the polar solvent, such as water, through a third or fourth addition port. By using different addition ports for the polar solvent and the alcohol or one or more bases, the polar solvent flow rate can be controlled, for example increased, without the need to change the flow rate of other ingredients in order to maintain the necessary molar flow ratio.

In practice, it can be desirable to rinse the microflow reactor before starting the reaction. The rinsing step can be performed again before taking the microflow reactor off line, when restarting the process after the microflow reactor has been off line, or both. Rinsing typically comprises allowing a solvent, typically the organic solvent or the polar solvent as described herein, to flow through the microflow reactor. The flow rate of the polar solvent during the rinsing step can be any suitable flow rate, which will depend on the volume of the microflow reactor. The rinsing step, when employed, is often performed for a length of time suitable to remove any salts, contaminants, or impurities that have accumulated within the microflow reactor. This time will vary depending on the volume of the microflow reactor, but is typically from 1 minute to 1 hour, and most often from 1 minute to 15 minutes. The solvent then exits the microflow reactor and can be collected from the exit port. The rinsing step is not needed in all cases.

A priming step can be also be performed before starting the reaction. If both rinsing and priming steps are employed, the priming step is typically performed after the rinsing step. The priming step typically comprises pumping the alcohol, which can optionally be dissolved in the polar solvent or the organic solvent, through the microflow reactor, including the mixing chamber, and then collecting it after it passes through the exit port. The alcohol that is used in the priming step is typically discarded. The flow rate of alcohol during the priming step can be the same as that discussed above with respect to the addition of alcohol during the reaction. The priming step can be conducted for any suitable length of time, typically from 1 minute to 1 hour, such as from 1 minute to 15 minutes.

Once the any rinsing or priming steps have been completed, the ingredients can be added to the mixing chamber of the microflow reactor under the conditions described herein and allowed to mix inside the mixing chamber to form a product stream. The product stream can then exit the mixing chamber through the exit port. It is often convenient to attach tubing to the exit port. The tubing can serve one or more purposes. For example, the tubing can function to cool the reaction mixture, to allow space for the reaction to complete, to transport the product stream to a desired location, for example, to collect the product or to act as a feed for another reactor, such as another microflow reactor, or any combination of the foregoing. The various ingredients can be pumped into the reactor using any suitable pump. For small scales and short run times, syringe pumps can be used. Other pumps, such as gear pumps, multi-piston pumps, and the like, may be suitable for larger scales or longer run times. After a brief initial startup time, the (alk)acrylic ester product in the product stream will be exiting the mixing chamber of the microflow reactor through the exit port simultaneously with the addition of the ingredients through the addition ports.

When the product stream exits the microflow reactor, it typically separates into two phases. The organic phase, which is typically a solution of the (alk)acrylic ester in the organic solvent, is easily separable from the polar solvent, typically water, which typically contains the salts, because the polar solvent is immiscible with the organic solvent. Thus, recovery of the product in this method can be easily achieved by separating the two phases and retaining the organic phase. This can be performed manually, such as by an extraction funnel, or in-line with a Dean-Starke trap or similar device.

Although the reaction of alcohol with (alk)acryloyl halide or 3-haloalkylcarboxyl halide is usually highly exothermic, it is typically not necessary to cool or otherwise adjust the temperature of the microflow reactor during the process described herein. Thus, the reaction can be carried out without any cooling of the microflow reactor, specifically without cooling the mixing chamber of the microflow reactor. Instead, the process can be carried out at room temperature without any temperature control of the microflow reactor. Room temperature is understood by the artisan, but typically includes those temperatures that are typical for a laboratory or production plant facility, such as 20° C. to 25° C.

The process described herein can provide a product stream containing (alk)acrylic ester in high yield. The yield can be measured as the percent composition of the (alk)acrylic ester in the product stream relative to the total amount of the solutes in the organic portion of the product stream. More specifically, the yield can be the percent composition of (alk)acrylic ester compared to all of the compounds other than the solvents that are detectable in the organic portion of the product stream by gas chromatography. When present, the organic byproduct is typically a reaction product of the polar solvent, typically water, with the (alk)acryloyl halide or 3-haloalkylcarboxyl halide. However, many (alk)acrylic acid or 3-haloalkanoic acid compounds are water soluble and therefore will not be present in the organic portion of the product stream. When 3-haloalkylcarbonylhalide is used, the organic byproducts can also include the 3-haloalkonate ester of the alcohol, which is typically not water soluble and therefore, if present at all, will usually be in the organic portion of the product stream.

Thus, the process described herein is considered to be industrially acceptable when the product stream contains (alk)acrylic ester in an amount of no less than 80 wt % based on the total weight of (alk)acrylic ester, alcohol, and organic byproducts in the product stream. Lower yields are not suitable for industrial purposes and are considered unacceptable. In many cases, the yield is even higher, though this is not required. In some cases the amount of (alk)acrylic ester is 85 wt % or greater, 90 wt % or greater, or even 95 wt % or greater, in each case based on the total weight (alk)acrylic ester, alcohol, and 3-haloalkanoate ester of the alcohol, in the product stream. The weights of these components of the product stream can be measured by any suitable means, for example, by gas chromatography. When gas chromatography is used, the compounds in the product stream can be identified by comparing their retention time to that of standards on the same column. The areas for the peaks can be calculated using standard software, or even manually, and then converted into concentration by using calibration curves. The calibration curves can be established by standard samples having known concentrations of the compounds. Other suitable means of determining the wt % of the various components of the product stream include liquid chromatography, such as HPLC, and mass spectrometry.

That such high yields of (alk)acrylic ester can be obtained under the reaction conditions discussed herein is surprising. (Alk)acryloyl halides and 3-haloalkylcarboxyl halides are well known to be highly reactive with polar solvents, such as water, to provide corresponding acids. Despite the expectation that the presence of a polar solvent like water would rapidly hydrolyze the (alk)acryloyl halide or 3-haloalkylcarboxyl halide, the process described herein uses a polar solvent, typically water, yet surprisingly hydrolysis is not the major reaction and high yields of product can be achieved. Further, the reaction between (alk)acryloyl halide or 3-haloalkylcarboxyl halide is known to be highly exothermic, thus requiring external cooling to avoid dangerous release of heat, unwanted side reactions, or both. Surprisingly, the method disclosed herein proceed in high yields even when performed at room temperature and without the use of a cooling device for the microflow reactor.

LIST OF ILLUSTRATIVE EMBODIMENTS

The following list illustrates particular embodiments of the present disclosure, but is not intended to be limiting. Other embodiments, not illustrated here, are also contemplated.

1. A method of making an (alk)acrylic ester comprising
    adding to a mixing chamber of a microflow reactor
        an alcohol,
        one or more bases that are sufficient to at least partially deprotonate the alcohol,
        a polar solvent,
        an (alk)acryloyl halide or a 3-haloalkylcarboxyl halide, and
        an organic solvent that is immiscible with the polar solvent in sufficient quantity to dissolve the (alk)acryloyl halide or a 3-haloalkylcarboxyl halide;
        wherein
        the molar flow ratio of the alcohol to the sum of all of the one or more bases is 1 to at least 1.1; and
    producing a product stream comprising one or more (alk)acrylic esters and one or more salts of the one or more bases; and wherein
    the polar solvent added to the mixing chamber is sufficient to dissolve substantially all of the at one or more salts; and
    the product stream having an organic portion and a polar portion, the organic portion of the product stream comprising the (alk)acrylic ester in an amount of at least 80 wt % based on the total weight of the solutes in the organic portion of the product stream.
1a. The method of embodiment 1, wherein amount of (alk)acrylic ester is based on the total weight of the solutes of the organic portion of the product stream that are detectable by gas chromatography.
1b. The method of embodiment 1, wherein the product stream comprises the (alk)acrylic ester in an amount of at least 85 wt % based on the total weight of the (alk)acrylic ester, the alcohol, and organic byproducts in the product stream.
1c. The method of embodiment 1, wherein the product stream comprises the (alk)acrylic ester in an amount of at least 90 wt % based on the total weight of the (alk)acrylic ester, the alcohol, and organic byproducts in the product stream.
1d. The method of embodiment 1, wherein the product stream comprises the (alk)acrylic ester in an amount of at least 95 wt % based on the total weight of the (alk)acrylic ester, the alcohol, and organic byproducts in the product stream.
2. The method of any of the preceding embodiments 1, wherein
    the polar solvent comprises water, methanol, ethanol, propanol, or a mixture thereof.
3. The method of embodiment 2, wherein the propanol is n-propanol or iso-propanol.
4. The method of any of embodiments 1-2, wherein the polar solvent comprises water.
5. The method of any of embodiments 1-2 or 4, wherein the polar solvent is water.
5a. The method of embodiment 5, wherein the polar solvent is deionized water.
6. The method of any of the preceding embodiments, wherein the alcohol comprises a monoalcohol having only one hydroxy radical.
7. The method of any of the preceding embodiments, wherein the alcohol has a molecular weight less than 1 kiloDalton.
8. The method of any of the preceding embodiments, wherein the alcohol has a molecular weight less than 950 Daltons.
9. The method of any of the preceding embodiments, wherein the alcohol has a molecular weight less than 900 Daltons.
10. The method of any of the preceding embodiments, wherein the alcohol has a molecular weight less than 850 Daltons.
11. The method of any of the preceding embodiments, wherein the alcohol has a molecular weight less than 800 Daltons.
12 The method of any of the preceding embodiments, wherein the alcohol has a molecular weight less than 750 Daltons.
13. The method of any of the preceding embodiments, wherein the alcohol has a molecular weight less than 700 Daltons.
14. The method of any of the preceding embodiments, wherein the alcohol has a molecular weight less than 650 Daltons.
15. The method of any of the preceding embodiments, wherein the alcohol has a molecular weight less than 600 Daltons.
16. The method of any of the preceding embodiments, wherein the alcohol has a molecular weight less than 550 Daltons.
17. The method of any of the preceding embodiments, wherein the alcohol has a molecular weight less than 500 Daltons.
18. The method of any of the preceding embodiments, wherein the alcohol has a molecular weight less than 450 Daltons.
19 The method of any of the preceding embodiments, wherein the alcohol has a molecular weight less than 400 Daltons.
20. The method of any of the preceding embodiments, wherein the alcohol has a molecular weight less than 350 Daltons.
21. The method of any of the preceding embodiments, wherein the alcohol has a molecular weight less than 300 Daltons.
22. The method of any of the preceding embodiments, wherein the alcohol has a molecular weight less than 250 Daltons.

23. The method of any of the embodiments 1-7, wherein the alcohol is 1-octanol.
24. The method of any of the embodiments 1-7, wherein the alcohol is isooctyl alcohol.
25. The method of any of the embodiments 1-7, wherein the alcohol is 2-ethyl hexyl alcohol.
26. The method of any of the embodiments 1-7, wherein the alcohol is citronellol.
27. The method of any of the embodiments 1-7, wherein the alcohol is 2-octyldodecanol.
28. The method of any of the embodiments 1-7, wherein the alcohol is 2-hexyldecanol.
29. The method of any of the embodiments 1-7, wherein the alcohol is 4-hydroxybenzophenone.
29a. The method of any of the embodiments 1-7, wherein the alcohol is 4-phenoxyphenol or 3-phenoxyphenol.
29b. The method of any of embodiments 1-5 or 7-22, wherein the alcohol comprises a poly alcohol having more than one hydroxy radical.
30. The method of any of the preceding embodiments, wherein the one or more bases comprises at least one of triethyl amine, dimethyl amine, trimethyl amine, methyldiethyl amine, alkali metal hydroxide, and alkali earth metal hydroxide.
30a. The method of any of the preceding embodiments, wherein the one or more bases comprises triethyl amine.
31. The method of any of the preceding embodiments, wherein the one or more bases comprises potassium hydroxide, sodium hydroxide, or a mixture thereof.
32. The method of any of the preceding embodiments, wherein the step of adding one or more bases to the mixing chamber of a microflow reactor comprises adding a solution of at least one of the one or more bases in the polar solvent to the mixing chamber of the microflow reactor.
33. The method of any of the preceding embodiments, wherein the step of adding the alcohol to the mixing chamber of a microflow reactor comprises adding a solution of the alcohol in the polar solvent to the mixing chamber of the microflow reactor.
34. The method of any of the preceding embodiments, wherein the step of adding the alcohol to the mixing chamber of the microflow reactor comprises adding at least two different alcohols to the mixing chamber of the microflow reactor.
35. The method of any of the preceding embodiments, wherein the (alk)acryloyl halide or 3-haloalkylcarboxyl halide is (alk)acryloyl halide.
36. The method of embodiment 35, wherein the (alk)acryloyl halide comprises an alkyl group that is C10 or less.
37. The method of embodiment 35, wherein the (alk)acryloyl halide comprises an alkyl group that is C9 or less.
38. The method of embodiment 35, wherein the (alk)acryloyl halide comprises an alkyl group that is C8 or less.
39. The method of embodiment 35, wherein the (alk)acryloyl halide comprises an alkyl group that is C7 or less.
40. The method of embodiment 35, wherein the (alk)acryloyl halide comprises an alkyl group that is C6 or less.
41. The method of embodiment 35, wherein the (alk)acryloyl halide comprises an alkyl group that is C5 or less.
42. The method of embodiment 35, wherein the (alk)acryloyl halide comprises an alkyl group that is C4 or less.
43. The method of embodiment 35, wherein the (alk)acryloyl halide comprises an alkyl group that is C3 or less.
44. The method of embodiment 35, wherein the (alk)acryloyl halide comprises an alkyl group that is C2 or less.
45. The method of embodiment 35, wherein the (alk)acryloyl halide is acryloyl halide or methacryloyl halide.
46. The method of any of embodiments 35-45, wherein the halide of the (alk)acryloyl halide is chloride.
47. The method of any of the preceding embodiments, wherein the (alk)acryloyl halide is acryloyl chloride or methacryloyl chloride.
48. The method of any of the preceding embodiments, wherein the (alk)acryloyl halide is acryloyl chloride.
49. The method of any of the preceding embodiments, wherein the (alk)acryloyl halide is methacryloyl chloride.
50. The method of any of embodiments 1-35, wherein the (alk)acryloyl halide or 3-haloalkylcarboxyl halide is 3-haloalkylcarboxyl halide.
51. The method of embodiment 50, wherein the halo group of the 3-haloalkylcarboxyl halide is chloro.
52. The method of embodiment 50 or 51, wherein the haloalkyl group is C30 or less.
53. The method of embodiment 52, wherein the haloalkyl group is C25 or less.
54. The method of embodiment 53, wherein the haloalkyl group is C24 or less.
55. The method of embodiment 54, wherein the haloalkyl group is C22 or less.
56. The method of embodiment 55, wherein the haloalkyl group is C20 or less.
57. The method of embodiment 56, wherein the haloalkyl group is C18 or less.
58. The method of embodiment 57, wherein the haloalkyl group is C16 or less.
59. The method of embodiment 58, wherein the haloalkyl group is C12 or less.
60 The method of embodiment 59, wherein the haloalkyl group is C10 or less.
61. The method of embodiment 60, wherein the haloalkyl group is C8 or less.
62. The method of embodiment 61, wherein the haloalkyl group is C7 or less.
63. The method of embodiment 62, wherein the haloalkyl group is C6 or less.
64. The method of embodiment 63, wherein the haloalkyl group is C5 or less.
65. The method of embodiment 64, wherein the haloalkyl group is C4 or less.
66. The method of embodiment 65, wherein the haloalkyl group is C3 or less.
67. The method of any of the preceding embodiments, wherein the halide of the 3-haloalkyl carboxyl halide is chloride.
67a. The method of any of the preceding embodiments, wherein the 3-haloalkyl carboxyl halide is 3-chloropropionyl chloride.
68. The method of any of the preceding embodiments, wherein the organic solvent comprises one or more of dichloromethane, ethyl acetate, butyl acetate, methyl ethyl ketone, or methyl butyl ketone.
69. The method of any of the preceding embodiments, wherein the organic solvent comprises dichloromethane.
70. The method of any of the preceding embodiments, wherein the organic solvent is dichloromethane.
70a. The method of any of the preceding embodiments, wherein the organic solvent comprises ethylacetate.
70b. The method of any of the preceding embodiments, wherein the organic solvent is ethylacetate.
71. The method of any of the preceding embodiments, wherein the step of adding the (alk)acryloyl halide or 3-haloalkyl carboxyl halide to the mixing chamber of the microflow reactor comprises adding a solution of the (alk)

acryloyl halide or 3-haloalkyl carboxyl halide in the organic solvent to the mixing chamber of the microflow reactor.

72. The method of any of the preceding embodiments, wherein the step of adding the alcohol to the mixing chamber of the microflow reactor comprises adding a mixture of the alcohol and the one or more bases to the mixing chamber of the microflow reactor through a first addition port.

73. The method of any of the preceding embodiments, wherein the step of adding the (alk)acryloyl halide or a 3-haloalkylcarboxyl halide to the mixing chamber of the microflow reactor comprises adding the (alk)acryloyl halide or a 3-haloalkylcarboxyl halide to the mixing chamber of the microflow reactor through a second addition port.

73a. The method of any of the preceding embodiments, wherein the step of adding the alcohol to the mixing chamber of the microflow reactor comprises adding a mixture of the alcohol, the polar solvent, and the one or more bases to the mixing chamber of the microflow reactor through a first addition port.

74. The method of any of the preceding embodiments, wherein the step of adding the (alk)acryloyl halide or a 3-haloalkylcarboxyl halide to the mixing chamber of the microflow reactor comprises adding a solution of the (alk)acryloyl halide or a 3-haloalkylcarboxyl halide in the organic solvent to the mixing chamber of the microflow reactor through a second addition port.

75. The method of any of the embodiments 1-70, wherein the mixing chamber of the microflow reactor comprises a first addition port, a second addition port, a third addition port, and a fourth addition port, and wherein the adding step comprises
    adding a mixture of the alcohol and base through the first addition port.

76. The method of any of embodiments 1-70 or 75, wherein the adding step comprises adding the (alk)acryloyl halide or a 3-haloalkylcarboxyl halide through the second addition port.

77. The method of any of embodiments 1-70 or 75-76, wherein the adding step comprises adding the polar solvent through the third addition port.

78. The method of any of embodiments 1-70 or 75-77, wherein the adding step comprises and adding the organic solvent through the fourth addition port.

79. The method of any of the preceding embodiments, wherein the molar flow ratio of the alcohol to the (alk)acryloyl halide or 3-haloalkylcarboxyl halide is 1 to at least 1.1.

80. The method of any of the preceding embodiments, wherein the molar flow ratio of the alcohol to the (alk)acryloyl halide or 3-haloalkylcarboxyl halide is 1 to at least 1.2.

81. The method of any of the preceding embodiments, wherein the molar flow ratio of the alcohol to the (alk)acryloyl halide or 3-haloalkylcarboxyl halide is 1 to at least 1.3.

82. The method of any of the preceding embodiments, wherein the molar flow ratio of the alcohol to the (alk)acryloyl halide or 3-haloalkylcarboxyl halide is 1 to at least 1.4.

83. The method of any of the preceding embodiments, wherein the molar flow ratio of the alcohol to the (alk)acryloyl halide or 3-haloalkylcarboxyl halide is 1 to at least 1.5.

84. The method of any of the preceding embodiments, wherein the molar flow ratio of the alcohol to the (alk)acryloyl halide or 3-haloalkylcarboxyl halide is 1 to at least 1.6.

85. The method of any of the preceding embodiments, wherein the molar flow ratio of the alcohol to the (alk)acryloyl halide or 3-haloalkylcarboxyl halide is 1 to at least 1.7.

86. The method of any of the preceding embodiments, wherein the molar flow ratio of the alcohol to the (alk)acryloyl halide or 3-haloalkylcarboxyl halide is 1 to at least 1.8.

87. The method of any of the preceding embodiments, wherein the molar flow ratio of the alcohol to the (alk)acryloyl halide or 3-haloalkylcarboxyl halide is 1 to at least 1.9.

88. The method of any of the preceding embodiments, wherein the molar flow ratio of the alcohol to the (alk)acryloyl halide or 3-haloalkylcarboxyl halide is 1 to at least 2.0.

89. The method of any of the preceding embodiments, wherein the molar flow ratio of the alcohol to the (alk)acryloyl halide or 3-haloalkylcarboxyl halide is 1 to at least 2.1.

90 The method of any of the preceding embodiments, wherein the molar flow ratio of the alcohol to the (alk)acryloyl halide or 3-haloalkylcarboxyl halide is 1 to at least 2.2.

91. The method of any of the preceding embodiments, wherein the molar flow ratio of the alcohol to the (alk)acryloyl halide or 3-haloalkylcarboxyl halide is 1 to at least 2.3.

92. The method of any of the preceding embodiments, wherein the molar flow ratio of the alcohol to the (alk)acryloyl halide or 3-haloalkylcarboxyl halide is 1 to at least 2.4.

93. The method of any of the preceding embodiments, wherein the molar flow ratio of the alcohol to the (alk)acryloyl halide or 3-haloalkylcarboxyl halide is 1 to at least 2.5.

94. The method of any of the preceding embodiments, wherein the molar flow ratio of the alcohol to the sum of all of the at least one bases is 1 to at least 1.5

95. The method of any of the preceding embodiments, wherein the molar flow ratio of the alcohol to the sum of all of the at least one bases is 1 to at least 1.8.

96. The method of any of the preceding embodiments, wherein the molar flow ratio of the alcohol to the sum of all of the at least one bases is 1 to at least 1.9.

97. The method of any of the preceding embodiments, wherein the molar flow ratio of the alcohol to the sum of all of the at least one bases is 1 to at least 2.0.

98. The method of any of the preceding embodiments, wherein the molar flow ratio of the alcohol to the sum of all of the at least one bases is 1 to at least 2.1.

99. The method of any of the preceding embodiments, wherein the molar flow ratio of the alcohol to the sum of all of the at least one bases is 1 to at least 2.2.

100. The method of any of the preceding embodiments, wherein the molar flow ratio of the alcohol to the sum of all of the at least one bases is 1 to at least 2.3.

101. The method of any of the preceding embodiments, wherein the molar flow ratio of the alcohol to the sum of all of the at least one bases is 1 to at least 2.4.

102. The method of any of the preceding embodiments, wherein the molar flow ratio of the alcohol to the sum of all of the at least one bases is 1 to at least 2.5.

103. The method of any of the preceding embodiments, wherein the microflow reactor is not temperature controlled during the method.

104. The method of any of the preceding embodiments, wherein the mixing chamber of the microflow reactor has an internal volume of no more than 5 mL.
105. The method of any of the preceding embodiments, wherein the mixing chamber of the microflow reactor has an internal volume of no more than 1 mL.
106. The method of any of the preceding embodiments, wherein the mixing chamber of the microflow reactor has an internal volume of no more than 800 µL.
107. The method of any of the preceding embodiments, wherein the mixing chamber of the microflow reactor has an internal volume of no more than 750 µL.
108. The method of any of the preceding embodiments, wherein the mixing chamber of the microflow reactor has an internal volume of no more than 600 µL.
109. The method of any of the preceding embodiments, wherein the mixing chamber of the microflow reactor has an internal volume of no more than 500 µL.
110. The method of any of the preceding embodiments, wherein the mixing chamber of the microflow reactor has an internal volume of no more than 400 µL.
111. The method of any of the preceding embodiments, wherein the mixing chamber of the microflow reactor has an internal volume of no more than 300 µL.
112. The method of any of the preceding embodiments, wherein the mixing chamber of the microflow reactor has an internal volume of no more than 250 µL.
113. The method of any of the preceding embodiments, wherein the mixing chamber of the microflow reactor has an internal volume of no more than 200 µL.
114. The method of any of the preceding embodiments, wherein the mixing chamber of the microflow reactor has an internal volume of no more than 100 µL.
115. The method of any of the preceding embodiments, wherein the mixing chamber of the microflow reactor has an internal volume of no more than 50 µL.
116. The method of any of the preceding embodiments, wherein the method further comprises a rinsing step that occurs before the adding step, the rinsing step comprising flowing a rinsing solvent through the mixing chamber of the microflow reactor and out of an exit port.
117. The method of embodiment 116, wherein the rinsing solvent comprises water, ethanol, ethanol, propanol, or a mixture thereof.
118. The method of embodiment 117, wherein the rinsing solvent is water.
119. The method of any of the preceding embodiments, wherein the rinsing solvent is selected to be the same as the polar solvent.
120. The method of any of the preceding embodiments, wherein the method further comprises a priming step that occurs before the adding step, the priming step comprising flowing the alcohol through the mixing chamber of the microflow reactor and out of an exit port.
121. The method of embodiment 120, wherein the priming step consists of flowing a solution of the alcohol through the mixing chamber of the microflow reactor and out of an exit port.
122. The method of embodiment 121, wherein the solution of alcohol comprises the alcohol and the polar solvent.
123. The method of embodiment 121 or 122, wherein the solution of alcohol comprises the alcohol, the polar solvent, and at least one of the one or more bases.
124. The method of any of embodiments 120-123, wherein the priming step takes place after a rinsing step.
125. The method of embodiment 124, wherein the rinsing step is the rinsing step of any of embodiments 116-119.

126. The method of any of the preceding embodiments, wherein a product stream comprising an (alk)acrylic ester exits the microflow reactor through an exit port.
127. The method of embodiment 126, wherein the product stream comprises a polar phase and an organic phase, the organic phase comprising the (alk)acrylic ester.
128. The method of embodiment 127, wherein the polar phase is an aqueous phase comprising the polar solvent.
129. The method of any of embodiments 127-128, wherein the method further comprises separating the polar phase from the organic phase.
130. The method of any of the preceding embodiments, wherein a product stream comprising the (alk)acrylic ester exits the mixing chamber of the microflow reactor through an exit port, and further comprising the step of feeding the product stream into another reaction vessel.
131. The method of any of the preceding embodiments, wherein the microflow reactor is an impinging flow reactor.
132. The method of any of the preceding embodiments, wherein the microflow reactor is not cooled by cooling equipment.
133. The method of any of the preceding embodiments, wherein the mixing chamber of the microflow reactor is not cooled by cooling equipment.
134. The method of any of the preceding embodiment, wherein the method is carried out at room temperature.

EXAMPLES

The following abbreviations are used in this section: NMR=nuclear magnetic resonance, mL=milliliters, µL=microliters, s=seconds, min=minutes, g=grams, µm=micrometers, mm=millimeters, m=meters, ppm=parts per million, mol=mole, mol %=mole percent, kPa=kilopascals. Abbreviations of materials used in this section, as well as descriptions of the materials, are provided in Table 1.

TABLE 1

| Material | Description |
| --- | --- |
| BP | 4-hydroxybenzophenone, available from Aldrich, Belgium |
| 3CPC | 3-chloropropionylchloride, available from Aldrich, Belgium |
| TEA | triethylamine, available from Aldrich, Belgium |
| DCM | dichloromethane, available from Aldrich, Belgium |
| Water | de-ionized water |
| ACL | acryloylchloride, available from ABCR, Germany |
| Isofol 20 | >97% 2-octyldodecanol, available from Sasol, Germany |
| Isofol 16 | >97% 2-hexyldecanol, available from Sasol, Germany |
| CiOH | citronellol, available from Aldrich, Belgium |
| OOH | 1-octanol, available from Aldrich, Belgium |
| EtOAc | ethyl acetate, available from Aldrich, Belgium |
| MAC | methacryloyl chloride, available from Aldrich, Belgium |
| NaOH | sodium hydroxide, available from Aldrich, Belgium |
| NMP | N-methylpyrrolidone, available from Aldrich, Belgium |

Microreactor A Description

Reactions for some examples described below were performed using components assembled from a microreactor kit, available under the trade designation "Labtrix Start 1805-L-2" from Chemtrix BV, United Kingdom. Two syringe pumps were used to inject reactant streams, contained in SGE 1000 µL gas-tight syringes, through 300 µm i.d. PEEK tubing into a reactor chip. The reactor chip was a glass microchip with channel diameter of 300 µm, available under the trade designation "Type 3223" from Chemtrix BV. The microchip was heated and cooled by a temperature controller available from Laird Technologies, UK. A backpressure regulator, optionally, was installed at the outlet of the reactor chip.

Microreactor B Description

Reactions for some examples described below were performed using a microreactor having a mixing device having five addition ports with an internal volume of approximately 23 μL available under the trade designation "IDEX 91" from ACHROM, Belgium. Syringe pumps, available under the trade designation Chemtrix Labtrix Start from Chemtrix BV, delivered at least two reactant streams from at least two gas-tight syringes, available under the trade designation "Hamilton Syringe I0 mL 1010 TLL no stop" available from Chemtrix BV, through PFA tubing with an inner diameter of 0.5 mm, available under the trade designation "IDEX 1512L" from Achrom, Belgium, to at least two addition ports of the mixing device using connectors available from Achrom. The at least two reactant streams combined within the internal volume of the mixing device where a product stream was formed. The product stream exited the mixing device through a product port and flowed through PFA tubing with an inner diameter of 1 mm, connected to the product port using connectors available from Achrom, Belgium, into a collection vessel.

Molar Ratio

The term "Molar Ratio" is used throughout this section to mean the ratio or ratios of moles of indicated reactants added to a vessel used to contain a batch reaction. For example, if 1 mole of Component C and 2 moles of Component D are added to a reaction vessel, the molar ratio of Component C to Component D is 1:2.

% Composition

The term "% Composition" is used throughout this section to mean the percent, by weight, of the specified compound in the organic portion of the product stream, with respect to the combination of all components identified in the organic portion of the product stream by gas chromatography (GC), excluding solvent. The concentrations were determined by GC, as described below, under "Characterization." Samples were collected from the organic layer in the collection vessel receiving the product stream during experiments. After initiating flow in an experiment, the first five or more reactor volumes of product stream were discarded and not included in the volume sampled for analysis.

Characterization

GC: The concentration of solutes in the product stream from the microreactor in experiments was determined using a gas chromatograph (GC) available under the trade designation "6890N" from Agilent Technologies, USA, using a flame ionization detector. The column used was a 95% polydimethylsiloxane/5% polydiphenylsiloxane, 30 m length, 0.32 mm diameter, 0.25 μm film thickness, available under the trade designation "HP-5" from Agilent Technologies, USA. Hydrogen was used as the carrier gas. Areas of peaks for compounds identified by retention time were converted to concentration values using calibration curves established for known concentrations of standards of the compounds.

NMR: Analysis by NMR was made using a Bruker Avance 300 Digital NMR spectrometer equipped with Bruker 5 mm BBFO 300 MHz Z-gradient high resolution-ATM probe. The samples were placed in NMR tubes available under the trade designation "WG-5M-ECONOMY" from Aldrich, Belgium. TMS (tetramethylsilane, available from Aldrich, Belgium) was added as a zero ppm reference. Proton NMR spectra were acquired using the following parameters:

Pulse Angle: 30°
Number of Scans: 128
Acquisition Time: 5.3 s
Relaxation time: 2.0 s Except where noted, NMR confirmed the identity of the desired products.

Comparative Example 1 (CE-1) Through Comparative Example 4 (CE-4)

CE-1 was performed using Microreactor A described above. A 20 bar backpressure regulator, available from Chemtrix BV, was installed. Syringe I contained OOH and syringe I contained ACL. Syringe I and syringe II contained sufficient contents to carry out CE-1 at the specified flow rates. The temperature of the reactor chip was controlled at 0° C. Before performing the reaction, the channel of the microreactor was rinsed with ethyl acetate. Following the rinse, the microreactor was primed with OOH using a flow rate of 20 μL/min for 5 min. When 5 min had elapsed, flow began of 1.1 μL/min from Syringe I and 0.9 μL/min from Syringe II into the reactor chip, providing a molar flow ratio of OOH:ACL of 1:1.5. After these conditions had been applied for 10 min, a sample was collected from the outlet of the reactor chip and analyzed by GC. For Comparative Examples CE-2, CE-3, and CE-4, the same procedure was followed, except that the reactor chip temperature was controlled as indicated in Table 2 below. Reaction products for CE-1 through CE-4 are provided in Table 2.

Comparative Example 5 (CE-5)

CE-5 was performed using Microreactor A described above, without the optional backpressure regulator installed. Syringe I contained 13 g OOH and 11.1 g TEA. Syringe II contained ACL. The reactor chip temperature was controlled at 25° C. The contents of syringe I were pumped to the reactor chip at a flow rate of 7.7 μL/min and the contents of syringe II at 2.3 μL/min. The molar flow ratios of OOH:ACL:TEA were 1:1.1:1.1. After starting the reaction, formation of white precipitate was noticed in the reactor chip. After approximately 2 min, pressure increase in the reactor chip was observed. After approximately 5 min, the reactor chip was completely blocked with white precipitate, preventing further measurement under these conditions. Syringe I contents and molar flow ratios for CE-5 are provided in Table 2.

Comparative Example 6 (CE-6)

CE-6 was performed using the equipment and procedure described for CE-5, except that syringe I contained a mixture of 13 g OOH, 11.1 g TEA and 12.4 g NMP, and flow rates were as indicated for CE-6 in Table 2. The molar flow ratios of OOH:ACL:TEA were 1:1.1:1.1. Precipitate in the reactor chip was observed after initiation of the flow or reactants to the reactor chip. The reactor chip was completely blocked with precipitate after approximately 10 min, preventing further measurement under these conditions. Syringe I contents and molar flow ratios for CE-6 are provided in Table 2.

Comparative Example 7 (CE-7)

CE-7 was performed using the equipment and procedure described for CE-6, except that DCM was used in place of NMP. The molar flow ratios of OOH:ACL:TEA were 1:1.0:

1.1. Precipitate in the reactor chip was observed after initiation of the flow or reactants to the reactor chip. The reactor chip was plugged by precipitate after approximately 10 min, preventing further measurement under these conditions. Syringe I contents and molar flow ratios for CE-7 are provided in Table 2.

For EX-2 through EX-17, the same procedure was followed but with syringe contents and flow rates as indicated in Table 3. Blend compositions, flow rates, molar flow ratios of BP:ACL:TEA, and % Composition are provided in Table 3.

TABLE 2

Amounts of BP, TEA, Solvent, ACL, and DCM are indicated in grams
Syringe I and Syringe II flow rates are indicated in μL/min

| Comparative Example | Reactor Chip Temperature (° C.) | Syringe I OOH | Syringe I TEA | Syringe I Solvent | Syringe I Flow Rate | Syringe II Flow Rate | Molar flow ratios (OOH:ACL:TEA) | % Composition |
|---|---|---|---|---|---|---|---|---|
| CE-1 | 0 | NR | 0 | 0 | 1.1 | 0.9 | 1:1.5:0 | 12% octylacrylate (OCA) 5% octyl 3-chloropropionate (OCP) 83% unreacted OOH |
| CE-2 | 20 | NR | 0 | 0 | 1.1 | 0.9 | 1:1.5:0 | 20% OCA 9% OCP 71% unreacted OOH |
| CE-3 | 60 | NR | 0 | 0 | 1.1 | 0.9 | 1:1.5:0 | 35% OCA 45% OCP 20% unreacted OOH |
| CE-4 | 100 | NR | 0 | 0 | 1.1 | 0.9 | 1:1.5:0 | 2% OCA 95% OCP 3% unreacted OOH |
| CE-5 | 25 | 13 | 11.1 | 0 | 7.7 | 2.3 | 1:1.1:1.1 | NM |
| CE-6 | 25 | 13 | 11.1 | NMP, 12.4 | 8.3 | 1.7 | 1:1.1:1.1 | NM |
| CE-7 | 25 | 13 | 11.1 | DCM, 12.4 | 8.3 | 1.7 | 1:1.0:1.1 | NM |

NR = not recorded,
NM = not measureable

Examples 1 Through 17 (EX-1 Through EX-17)

For EX-1, the following procedure was carried out using Microreactor B, described above, with the mixing device at ambient temperature. Syringe I contained 15 g BP, 22 g TEA, and 22 g water. Syringe II contained 3 g ACL and 20 g DCM. Each syringe was placed in a separate syringe pump and the pump speeds were controlled to deliver the blends at the flow rates indicated for EX-1 in Table 3 below. The two unused addition ports of the mixing device were sealed with plugs. The molar flow ratios of BP:ACL:TEA pumped to the mixing device were 1:1.1:2.9. Separation of aqueous phase and an organic phase was observed in the collection vessel. Analysis of the upper, aqueous phase by NMR indicated approximately 8 mol % of acrylic acid-TEA salt and approximately 92 mol % TEA-HCl salt. Analysis of the lower, organic phase by NMR indicated approximately 51 mol % 4-acryloxybenzophenone (ABP), approximately 0.01 mol % BP and approximately 42 mol % of the above mentioned TEA salts. Analysis of the organic layer by GC indicated 95% Composition of ABP and 2% of unreacted alcohol. After analysis, the organic layer was washed with water to remove salts and residual TEA.

Comparative Examples 8 Through 10 (CE-8 Through CE-10)

For CE-8, CE-9, and CE-10, the same procedure was followed as described for EX-1, but with syringe contents and flow rates as indicated in Table 3. Blend compositions, flow rates, molar flow ratios of BP:ACL:TEA, and % Composition are provided in Table 3.

Comparative Example 11 (CE-11)

CE-11 was performed using the procedure of EX-1, except that syringe I contained a blend of 15 g BP, 22 g TEA and 20 g water at the start of the experiment. This resulted in molar flow ratios of BP:ACL:TEA of 1:1.03:2.87. A white precipitate was observed in the tubing downstream of the mixing device outlet after initiation of flow of reactants to the mixing device, preventing measurement under these conditions.

TABLE 3

Amounts of BP, TEA, Water, ACL, and DCM are indicated in grams
Syringe I and Syringe II flow rates are indicated in mL/min

| Example | Syringe I BP | Syringe I TEA | Syringe I Water | Syringe II ACL | Syringe II DCM | Syringe I Flow Rate | Syringe II Flow Rate | Molar flow ratios (BP:ACL:TEA) | % Composition |
|---|---|---|---|---|---|---|---|---|---|
| EX-1 | 15 | 22 | 22 | 3 | 20 | 1.2 | 0.8 | 1:1.1:2.9 | 95 |
| EX-2 | 15 | 22 | 22 | 3 | 20 | 0.6 | 0.6 | 1:1.6:2.9 | 99 |
| EX-3 | 15 | 22 | 22 | 3 | 10 | 1.2 | 0.6 | 1:1.4:2.9 | 88 |
| EX-4 | 15 | 22 | 22 | 3 | 10 | 1.2 | 0.8 | 1:1.9:2.9 | 99 |
| EX-5 | 15 | 22 | 22 | 3 | 5 | 1.2 | 0.6 | 1:2.2:2.9 | 98 |
| EX-6 | 15 | 22 | 22 | 3 | 5 | 1.2 | 0.5 | 1:1.8:2.9 | 95 |
| EX-7 | 15 | 22 | 22 | 3 | 5 | 1.2 | 0.4 | 1:1.5:2.9 | 89 |
| EX-8 | 15 | 22 | 22 | 3 | 5 | 0.5 | 0.2 | 1:1.8:2.9 | 95 |

TABLE 3-continued

Amounts of BP, TEA, Water, ACL, and DCM are indicated in grams
Syringe I and Syringe II flow rates are indicated in mL/min

| Example | Syringe I BP | TEA | Water | Syringe II ACL | DCM | Syringe I Flow Rate | Syringe II Flow Rate | Molar flow ratios (BP:ACL:TEA) | % Composition |
|---|---|---|---|---|---|---|---|---|---|
| EX-9  | 15 | 22 | 22 | 3 | 5  | 1.0 | 0.4  | 1:1.8:2.9 | 97 |
| EX-10 | 15 | 22 | 22 | 3 | 5  | 2.0 | 0.8  | 1:1.8:2.9 | 98 |
| EX-11 | 15 | 22 | 22 | 3 | 5  | 4.0 | 1.6  | 1:1.8:2.9 | 99 |
| EX-12 | 15 | 22 | 22 | 3 | 5  | 5.0 | 2.0  | 1:1.8:2.9 | 95 |
| EX-13 | 20 | 20 | 20 | 3 | 20 | 0.6 | 0.6  | 1:1.2:2.0 | 99 |
| EX-14 | 20 | 20 | 20 | 3 | 20 | 0.8 | 0.8  | 1:1.2:2.0 | 89 |
| EX-15 | 20 | 20 | 20 | 3 | 20 | 1.0 | 1.0  | 1:1.2:2.0 | 84 |
| EX-16 | 20 | 22 | 20 | 3 | 20 | 0.6 | 0.6  | 1:1.3:2.2 | 88 |
| EX-17 | 15 | 22 | 22 | 3 | 20 | 2.4 | 1.6  | 1:1.1:2.9 | 92 |
| CE-8  | 15 | 22 | 22 | 3 | 20 | 4.8 | 3.2  | 1:1.1:2.9 | 75 |
| CE-9  | 15 | 22 | 22 | 3 | 20 | 9.6 | 6.4  | 1:1.1:2.9 | 66 |
| CE-10 | 15 | 22 | 22 | 3 | 5  | 1.0 | 0.18 | 1:0.8:2.9 | 74 |
| CE-11 | 15 | 22 | 20 | 3 | 20 | 1.2 | 0.8  | 1:1.0:2.9 | NM |

NM = not measureable
"% Composition" refers to the % composition of the 4-hydroxybenzophenone ester of acrylic acid Example 18 (EX-18)

EX-18 was performed using the procedure of EX-1, except that syringe II contained 3 g MAC and 20 g DCM, and flow rates were as indicated for EX-18 in Table 4 below. The resulting molar flow ratios of BP:MAC:TEA were 1:1.1:2.9. Analysis of the product stream indicated % Composition was 98%. Blend compositions, flow rates, the molar flow ratios of BP:ACL:TEA, and % Composition are provided in Table 4.

Example 19 (EX-19)

EX-19 was performed using the procedure of EX-1, except that three syringes were used: Syringe I contained 7.9 g BP, 7 g TEA, and 3 g DCM; syringe II contained ACL; syringe III contained water. The amount of ACL and water placed in syringes was each sufficient carry out the experiment at the specified flow rates. One unused addition port of the mixing device was sealed with a plug. Syringe pumps were used to deliver the flow rates indicated in Table 5 from the three syringes to the mixing device. Separation of aqueous phase and an organic phase was observed in the collection vessel. Analysis by GC indicated the organic layer was 92% ABP. Blend compositions, flow rates, the molar flow ratio of BP:ACL, and % Composition are provided in Table 5.

Example 20 (EX-20)

EX-20 was performed using the procedure of EX-1, except that syringe I contained 15 g BP, 7.5 g TEA, 3 g NaOH, and 22 g water, syringe II contained 6 g ACl and 12 g EtOAc, and flow rates were as indicated in Table 6 below. The molar flow ratio of BP:ACL was 1:1.6. Analysis by GC indicated the organic layer was 97% ABP. Blend compositions, flow rates, the molar flow ratios of BP:ACL TEA: NaOH, and % Composition are provided in Table 6.

TABLE 4

Amounts of BP, TEA, Water, MAC, and DCM are indicated in grams
Syringe I and Syringe II flow rates are indicated in mL/min

| Example | Syringe I BP | TEA | Water | Syringe II MAC | DCM | Syringe I Flow Rate | Syringe II Flow Rate | Molar flow ratios (BP:MAC:TEA) | % Composition |
|---|---|---|---|---|---|---|---|---|---|
| EX-18 | 15 | 22 | 22 | 3 | 20 | 0.8 | 1 | 1:1.1:2.9 | 98 |

"% Composition" refers to the % composition of the 4-hydroxybenzophenone ester of methacrylic acid

TABLE 5

Amounts of BP, DCM, TEA, ACL, and water are indicated in grams
Syringe I and Syringe II flow rates are indicated in mL/min

| Example | Syringe I BP | DCM | TEA | Syringe II ACL | Syringe III Water | Syringe I Flow Rate | Syringe II Flow Rate | Syringe III Flow Rate | Molar flow ratio (BP:ACL:TEA) | % Composition |
|---|---|---|---|---|---|---|---|---|---|---|
| EX-19 | 7.9 | 3 | 7 | NR | NR | 0.6 | 0.1 | 0.3 | 1:1.1:1.7 | 92 |

NR = not recorded
"% Composition" refers to the % Composition of the 4-hydroxybenzophenone ester of acrylic acid

TABLE 6

Amounts of BP, NaOH, TEA, Water, ACL, and EtOAc are indicated in grams
Syringe I and Syringe II flow rates are indicated in mL/min

| Example | Syringe I | | | | Syringe II | | Syringe I Flow Rate | Syringe II Flow Rate | Molar flow ratio (BP:ACL:TEA:NaOH) | % Composition |
| --- | --- | --- | --- | --- | --- | --- | --- | --- | --- | --- |
| | BP | NaOH | TEA | Water | ACL | EtOAc | | | | |
| EX-20 | 15 | 3 | 7.5 | 22 | 6 | 12 | 1 | 0.5 | 1:1.6:1:1 | 97 |

"% Composition" refers to the % Composition of the 4-hydroxybenzophenone ester of acrylic acid

Example 21 (EX-21)

EX-21 was carried out using Microreator B. For EX-21, syringe I contained 3 g of Isofol 20 and 1.5 g TEA. Syringe II contained ACL. Syringe III contained water. Syringe IV contained DCM. The amount of ACL, water, and DCM in syringes II, III, and IV was each sufficient carry out the experiment at the specified flow rates. The outlet each of the four syringes was connected to the mixing device by PFA tubing. Syringe pumps were used to deliver the contents of the syringes at a flow rate of 0.2 mL/min for each syringe. The molar flow ratios of Isofol 20:ACL:TEA were 1:1.1:1.6. The % Composition for EX-21 is provided in Table 7 below.

Examples 22 Through 26 (EX-22 Through EX-26)

EX-22 was carried out using Microreactor B. For EX-22, syringe I contained 15 g BP, 33 g TEA, and 33 g water. Syringe II contained 4.2 g 3CPC and 20 g DCM. Each syringe was placed in a separate syringe pump and the pump speeds were controlled to deliver the blends at the flow rates indicated for EX-22 in Table 8 below. The two unused addition ports of the mixing device were sealed with plugs. Separation of aqueous phase and an organic phase was observed in the collection vessel. Analysis of the upper, aqueous phase by NMR indicated approximately 8 mol % of acrylic acid-TEA salt and approximately 92 mol % TEA-HCl salt. Analysis of the lower, organic phase by NMR indicated approximately 51 mol % ABP, approximately 0.01 mol % BP and approximately 42 mol % of the above mentioned TEA salts. Analysis by GC indicated the organic layer was 98% ABP and 2% unreacted alcohol. After analysis, the organic layer was washed with water to remove salts and residual TEA.

For EX-23 through EX-26, the same procedure was followed as described for EX-22, except that flow rates were as indicated in Table 8. Blend compositions, flow rates, and % Composition are provided in Table 8.

Comparative Example 12 (CE-12)

For CE-12, the same procedure was followed as described for EX-22, but with 30 g water added to syringe I and with the syringe pumps set to apply the flow rates indicated in Table 8 to syringe I and syringe II. However, soon after initiation of flow from the syringes, inconsistent flow was observed from both syringes due to observed precipitated salts. The molar flow ratios of BP:TEA:3CPC provided for CE-12 in Table 8 were calculated from the set flow rates. The % Composition for CE-12 is provided in Table 8.

TABLE 7

Amounts of Alcohol and TEA are indicated in grams
Syringe I, II, III, and IV flow rates are indicated in mL/min

| Example | Syringe I | | Syringe II | Syringe III | Syringe IV | Syringe I, II, III, IV Flow Rate | Molar flow ratio (Alcohol:ACL:TEA) | % Composition |
| --- | --- | --- | --- | --- | --- | --- | --- | --- |
| | Alcohol | TEA | ACL | Water | DCM | | | |
| EX-21 | Isofol 20, 3 | 1.5 | NR | NR | NR | 0.2 | 1:1.1:1.6 | 87[1] |

[1]% Composition for EX-21 is of the 2-octyldodecyl ester of acrylic acid

TABLE 8

Amounts of BP, TEA, Water, 3CPC, and DCM are indicated in grams
Syringe I and Syringe II flow rates are indicated in mL/min

| Example or Comparative Example | Syringe I | | | Syringe II | | Syringe I Flow Rate | Syringe II Flow Rate | Molar flow ratio (BP:3CPC:TEA) | % Composition |
| --- | --- | --- | --- | --- | --- | --- | --- | --- | --- |
| | BP | TEA | Water | 3CPC | DCM | | | | |
| EX-22 | 15 | 33 | 33 | 4.2 | 20 | 1.2 | 0.8 | 1:1.5:4.3 | 98 |
| EX-23 | 15 | 33 | 33 | 4.2 | 20 | 0.8 | 0.6 | 1:1.6:4.3 | 90.1 |
| EX-24 | 15 | 33 | 33 | 4.2 | 20 | 2.4 | 1.6 | 1:1.5:4.3 | 90.1 |
| EX-25 | 15 | 33 | 33 | 4.2 | 20 | 2.4 | 1.8 | 1:1.6:4.3 | 98 |
| EX-26 | 15 | 33 | 33 | 4.2 | 20 | 2.4 | 1.8 | 1:1.6:4.3 | 98.6 |
| CE-12 | 15 | 33 | 30 | 4.2 | 20 | 2.4 | 1.4 | 1:1.2:4.3 | 72 |

"% Composition" refers to the % Composition of the 4-hydroxybenzophenone ester of acrylic acid

Examples 27 and 28 (EX 27 and EX 28)

For EX 27 the same procedure was used as for EX-22, except that the mixing device was cooled by immersion in an ice water bath and the flow rates for syringe I and syringe II were as indicated in Table 10 below. The temperature measured outside the mixing device using a type K digital thermometer available under the trade designation C.A. 860 from Chauvin Arnoux, France, was 5° C. before the start of flow of reactants. The highest temperature measured outside the mixing device during the experiment was 27° C. For EX 28, the same procedure was used as for EX 27, except that the mixing device was heated by immersion in an oil bath held at 80° C., as measured with the above mentioned thermometer, and the flow rates for syringe I and syringe II were as indicated for EX 28 in Table 10. The highest temperature measured outside the mixing device during the experiment was 80° C. The molar flow ratios, maximum temperatures reached and % Composition are provided in Table 9.

TABLE 9

Amounts of BP, TEA, Water, 3CPC, and DCM are indicated in grams
Syringe I and Syringe II flow rates are indicated in mL/min

| Example | Syringe I | | | Syringe II | | Syringe I Flow Rate | Syringe II Flow Rate | Molar flow ratio (BP:3CPC:TEA) | Maximum Temperature Reached (° C.) | % Composition |
|---|---|---|---|---|---|---|---|---|---|---|
| | BP | TEA | Water | 3CPC | DCM | | | | | |
| EX 27 | 15 | 33 | 33 | 4.2 | 20 | 0.8 | 0.6 | 1:1.1:3 | 27 | 96 |
| EX 28 | 15 | 33 | 33 | 4.2 | 20 | 0.05 | 0.05 | 1:1.1:1.8 | 80 | 86 |

"% Composition" is the % Composition of the 4-hydroxybenzophenone ester of acrylic acid

Comparative Examples 13 Through 15 (CE-13 Through CE-15)

For Comparative CE-13, the following procedure was carried out at ambient temperature. Into a 100 mL glass bottle, placed on a magnetic stir plate and purged with nitrogen, were placed: a magnetic stir bar, 2 g (0.01 mol) BP and 4.5 g TEA. The mixture was stirred for 5 min at; a yellow slurry was obtained. Then, 4.5 g water was added; after 15 min, a clear, yellow-brown solution was obtained. Then, 3 g DCM was added with 5 min mixing. Then, 13 g of 3CPC were added dropwise with continuous stirring to control the exotherm to about 40° C. The reaction was continued for 30 min. Then, stirring was stopped and the two phase system was allowed to separate. The molar ratio of BP:3CPC:TEA was 1:1.1:4.4. The top, organic phase was analyzed by GC. The concentration of acrylate was 51.3%.

For CE-14, the same procedure was used as for CE-13, except that CiOH was used in place of BP. The molar ratio of CiOH:3CPC:TEA was 1:1.1:4.4. Analysis of the top, organic phase by GC indicated concentration of the acrylate formed from CiOH was 42%.

For CE-15, the same procedure was used as for CE-13, except that Isofol 16 was used in place of BP. The molar ratio of Isofol 16:3CPC:TEA was 1:1.1:4.4. Analysis of the top, organic phase by GC indicated concentration of the acrylate formed from Isofol 16 was 34%.

What is claimed is:

1. A method of making an (alk)acrylic ester comprising adding to a mixing chamber of a microflow reactor
   an alcohol,
   one or more bases that are sufficient to at least partially deprotonate the alcohol,
   a polar solvent,
   an (alk)acryloyl halide or a 3-haloalkylcarboxyl halide, and
   an organic solvent that is immiscible with the polar solvent in sufficient quantity to dissolve the (alk) acryloyl halide or a 3-haloalkylcarboxyl halide; wherein
   the molar flow ratio of the alcohol to the sum of all of the one or more bases is 1 to at least 1.1; and
   producing a product stream comprising one or more (alk)acrylic esters and one or more salts of the one or more bases; wherein
   the polar solvent added to the mixing chamber is sufficient to dissolve substantially all of the at one or more salts; and
   the product stream having an organic portion and a polar portion, the organic portion comprises the (alk)acrylic ester in an amount of at least 80 wt % based on the total weight of the solutes in the organic portion of the product stream.

2. The method of claim 1, wherein
the polar solvent comprises water.

3. The method of claim 1, wherein
the mixing chamber of the microflow reactor comprises an exit port;
wherein the method further comprises a step of removing the (alk)acrylic ester from the exit port simultaneously with the adding step.

4. The method of claim 1, wherein
the one or more bases are soluble in the polar solvent, the alcohol, or both and are selected from amines, alkali metal hydroxides, alkali earth metal hydroxides, and combinations thereof.

5. The method of claim 4, wherein the one or more bases comprises triethyl amine.

6. The method of claim 1, wherein the mixing chamber of the microflow reactor comprises a first addition port and a second addition port, and wherein the adding step comprises
adding a mixture of the alcohol and the one or more bases through the first addition port; and
adding the (alk)acryloyl halide or a 3-haloalkylcarboxyl halide through the second addition port.

7. The method of claim 6, wherein
adding the mixture of the alcohol and the base through the first addition port comprises adding a mixture of the alcohol, the base, and the polar solvent through the first addition port; and
adding the (alk)acryloyl halide or a 3-haloalkylcarboxyl halide through the second addition port comprises adding a mixture of the organic solvent and the (alk) acryloyl halide or a 3-haloalkylcarboxyl halide through the second addition port.

8. The method of claim 1, wherein the mixing chamber of the microflow reactor comprises a first addition port, a second addition port, a third addition port, and a fourth addition port, and wherein the adding step comprises
- adding a mixture of the alcohol and base through the first addition port;
- adding the (alk)acryloyl halide or a 3-haloalkylcarboxyl halide through the second addition port;
- adding the polar solvent through the third addition port; and
- adding the organic solvent through the fourth addition port.

9. The method of claim 1, wherein the molar flow ratio of the alcohol to the (alk)acryloyl halide or 3-haloalkylcarboxyl halide is 1 to at least 1.1.

10. The method of claim 1, wherein the (alk)acryloyl halide or a 3-haloalkylcarboxyl halide is 3-chloropropionylchloride.

11. The method of claim 1, wherein the (alk)acryloyl halide or a 3-haloalkylcarboxyl halide is an (alk)acrylyl halide.

12. The method of claim 1, wherein the (alk)acryloyl halide or a 3-haloalkylcarboxyl halide is acryloyl chloride or methacryloyl chloride.

13. The method of claim 1, wherein the organic solvent is selected from dichloromethane, ethyl acetate, butyl acetate, methyl ethyl ketone, methyl butyl ketone.

14. The method of claim 1, wherein the microflow reactor is not temperature controlled during the method.

15. The method of claim 1, wherein the mixing chamber of the microflow reactor has an internal volume of no more than 1 mL.

* * * * *

UNITED STATES PATENT AND TRADEMARK OFFICE
CERTIFICATE OF CORRECTION

PATENT NO. : 10,308,584 B2
APPLICATION NO. : 16/079161
DATED : June 4, 2019
INVENTOR(S) : Rudolf Dams et al.

It is certified that error appears in the above-identified patent and that said Letters Patent is hereby corrected as shown below:

In the Specification

Column 1,
Line 32, after "scale" insert -- . --.

Column 3,
Line 6, delete "dividing" and insert -- multiplying --, therefor.
Line 13, after "is" delete "1 to 1".
Line 13, delete ")/(" and insert -- )( --, therefor.
Line 14, delete "))." and insert -- )) = 2:8 = 1:4. --, therefor.
Line 21, after "is" delete "2 to 1".
Line 22, delete ")/(" and insert -- )( --, therefor.
Line 23, delete ")/(" and insert -- )( --, therefor.
Line 23, delete "))." and insert -- )) = 4:8 = 1:2. --, therefor.

Column 9,
Line 32, after "can" delete "be".

Column 10,
Line 41, delete "3-haloalkonate" and insert -- 3-haloalkanoate --, therefor.

Column 24,
Line 40, delete "BP:ACL TEA:" and insert -- BP:ACL:TEA --, therefor.

Column 25,
Line 14, delete "Microreator" and insert -- Microreactor --, therefor.

Signed and Sealed this
Sixth Day of August, 2019

Andrei Iancu
*Director of the United States Patent and Trademark Office*